ABSTRACT

United States Patent [19]
Burk et al.

[11] 4,049,694
[45] Sept. 20, 1977

[54] 3-(4-(((TRICHLOROETHENYL)THIO)-PHENYL)SULFONYL)-2-PROPENENITRILE

[75] Inventors: George A. Burk, Bay City; Christian T. Goralski; Craig E. Mixan, both of Midland, all of Mich.

[73] Assignee: The Dow Chemical Company, Midland, Mich.

[21] Appl. No.: 760,220

[22] Filed: Jan. 10, 1977

[51] Int. Cl.$^2$ .......................................... C07C 121/70
[52] U.S. Cl. ................................ 260/465 G; 424/304
[58] Field of Search .................................... 260/465 G

[56] References Cited

U.S. PATENT DOCUMENTS

| | | | |
|---|---|---|---|
| 3,159,532 | 12/1964 | Heininger et al. | 424/304 |
| 3,541,119 | 11/1970 | Richter et al. | 260/397.6 |
| 3,821,399 | 6/1974 | Richter | 424/304 |

Primary Examiner—Dolph H. Torrence
Attorney, Agent, or Firm—Theodore Post; C. Kenneth Bjork

[57] ABSTRACT

The title compound is prepared by reacting trichloroethenylthiophenylsulfonyl chloride with acrylonitrile in the presence of a small amount of cupric chloride, acetonitrile and triethylamine hydrochloride, recovering the product from the reaction medium.

1 Claim, No Drawings

3-(4-(((TRICHLOROETHENYL)THIO)PHENYL)-SULFONYL)-2-PROPENENITRILE

DESCRIPTION OF CLOSEST KNOWN PRIOR ART

S. A. Heininger, in U.S. Pat. No. 3,159,532, patented Dec. 1, 1964, discloses arylsulfonyl alkenenitriles such as 3-(4-bromophenylsulfonyl)acrylonitrile, halo analogs thereof and alkyl homologs thereof. The compounds are said to inhibit the growth of microorganisms. S. U. K. A. Richter et al., in U.S. Pat. No. 3,541,119, patented Nov. 17, 1970, disclose unsaturated sulfones such an benzenesulfonylacrylonitrile, and related compounds wherein the benzene nucleus may have halo, lower alkyl or p-acetamido substitution. The compounds are said to have bioactive properties. S. U. K. A. Richter, in U.S. Pat. No. 3,821,399, patented June 28, 1974, discloses substituted phenylsulfonylacrylonitriles wherein the phenyl nucleus contains an amino, an acylamido or a nitrile group, and, optionally, a lower alkyl group. The compounds are said to prevent the growth of microorganisms.

SUMMARY OF THE INVENTION 3-(4-(((Trichloroethenyl)thio)phenyl)sulfonyl)-2-propenenitrile, hereinafter referred to as "Compound," is prepared by reacting trichloroethenylthiophenylsulfonyl chloride with excess acrylonitrile in the presence of cupric chloride, triethylamine hydrochloride and acetonitrile, and treating the resulting material with triethylamine according to the following equation:

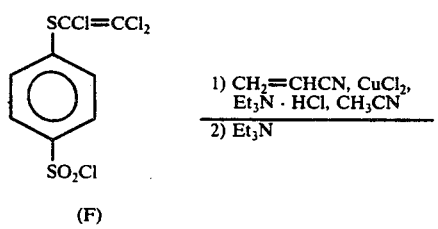

In practice, the trichloroethenylthiophenylsulfonyl chloride is placed in a pressure vessel with cupric chloride, a catalytic amount of triethylamine hydrochloride, a substantially equimolar proportion of acrylonitrile and a small proportion of acetonitrile. After cooling in a Dry Ice®bath, the vessel is evacuated, warmed to room temperature and immersed in an oil bath at about 110° C until reaction is substantially complete, approximately 8–12 hours. The solvent is then removed under reduced pressure and the residue is treated with triethylamine in benzene. The precipitated triethylamine hydrochloride is removed, the remaining liquor is washed with water, dried over desiccant-grade magnesium sulfate and decolorized with charcoal. Evaporation of the benzene and recrystallization from methanol gives Compound as white crystals, melting at 116° C.

DESCRIPTION OF SOME PREFERRED EMBODIMENTS

The following additional description and example further describe the invention and the manner and process of making and using it to enable the art skilled to make and use the same and set forth the best mode contemplated by the inventors of carrying out the invention.

Compound has antimicrobial activity. When evaluated in a conventional in vitro agar Petri dish dilution test for determining bactericidal and fungicidal activity, Compound gave 100 percent growth inhibition of the following organisms at the indicated concentrations in parts per million, indicated in the Table as minimum inhibitory concentration (MIC).

TABLE

| Compound | Sa* | Bs | Ca | Cp | Ts | Ap | Ci | Tm | Pc | Af | An |
|---|---|---|---|---|---|---|---|---|---|---|---|
| 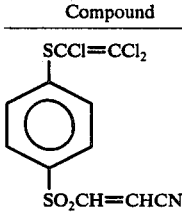 | 500 | 500 | 50 | 10 | 50 | 10 | 5 | 5 | 5 | 50 | 50 |

*Sa = S. aureus
Bs = B. subtilis
Ca = C. albicans
Cp = C. pelliculosa
Ts = Torulopsis Species
Ap = A. pullulans
Ci = C. ips
Tm = T. mentagrophytes
Pc = P. chrysogenum
Af = A. fumigatus
An = A. niger

EXAMPLE 3-(4-((Trichloroethenyl)thio)phenyl)sulfonyl)-2-propenenitrile

A. 2,2-Dichloro-1,1-difluorothiophenoxyethane

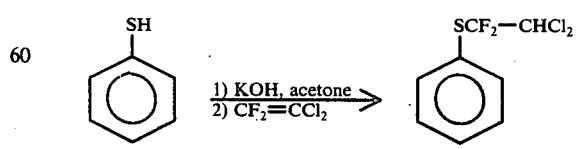

One mole (110 g) of thiophenol in 300 ml of dry acetone was treated with 11.2 g (0.21 mol) of powdered 85 percent KOH, and gaseous 1,1-difluoro-2,2-dichloroethene was introduced at 10° C at such a rate that the temperature was maintained below 12° C. After 111 g (0.84 mol) had been introduced (1½ hours), the reaction mixture was stirred in an ice bath overnight, and poured into ice water. The organic layer was separated, washed with water, and dried. Distillation through a vigreux column at 8 mm provided a 125 g (61% yield) of colorless liquid, boiling at 135° C. This material was identified as 2,2-dichloro-1,1-difluorothiophenoxyethane.

B. Trichloroethenylthiophenylsulfonyl chloride

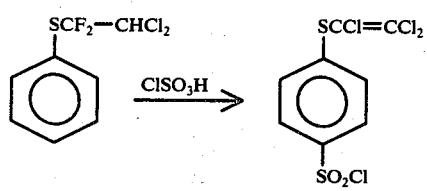

Forty grams (0.168 mole) of the preceding product was slowly added to 100 ml of chlorosulfonic acid (1.5 moles) at 10°-15° C with rapid stirring. After two hours, the reaction mixture was cautiously poured over crushed ice. The organic layer was recovered in methylene chloride and dried. Removal of the solvent under reduced pressure gave 46 g (0.136 mol, 80% yield) of a pale yellow oil. This oil consisted of a mixture of a major proportion of trichloroethenylthiophenylsulfonyl chloride and a minor proportion of the corresponding sulfonyl fluoride as determined by mass spectrometry.

C. 3-(4-(((Trichloroethenyl)thio)phenyl)sulfonyl)-2-propenenitrile

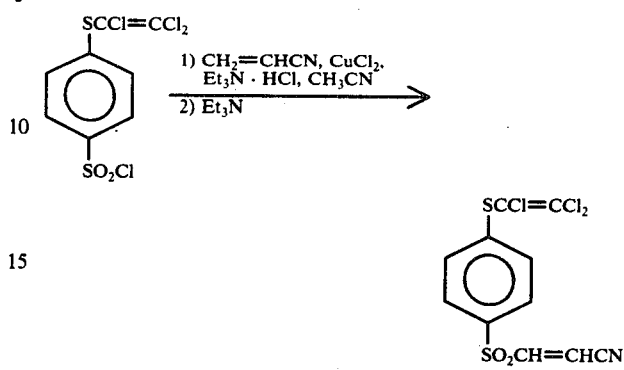

Thirty grams (0.123 mole) of the preceding product was placed in a 100 ml pressure vessel with 0.18 g (0.0013 mole) of cupric chloride, 0.30 g (0.0022 mole) of triethylamine hydrochloride, 13.0 g (0.25 mole) of distilled acrylonitrile and 2 ml (0.05 mole) of acetonitrile. After cooling in a Dry Ice®bath, the vessel was evacuated, warmed to room temperature, and immersed in an oil bath at 108° C overnight. The solvent was removed under reduced pressure, and, without purification or isolation, the residue was treated with 2 g (0.02 mole) of triethylamine in benzene. After removal of the precipitated amine hydrochloride, the liquor was washed with water, dried over magnesium sulfate, and decolorized with charcoal. Evaporation of the benzene and recrystallization from methanol provided 7.1 g (0.02 mole, 16% yield) of white crystals, mp 116° C.

Anal. Calcd for $C_{11}H_6Cl_3NO_2S_2$: C, 37.25; H, 1.72; N, 3.95; Cl, 30.00. Found: C, 37.17; H, 1.77; N, 4.02; Cl, 29.3.

What is claimed is:
1. The compound 3-(4-(((trichloroethenyl)thio)phenyl)sulfonyl)-2-propenenitrile.

* * * * *

UNITED STATES PATENT AND TRADEMARK OFFICE
CERTIFICATE OF CORRECTION

PATENT NO. : 4,049,694

DATED : September 20, 1977

INVENTOR(S) : George A. Burk, et al.

It is certified that error appears in the above-identified patent and that said Letters Patent are hereby corrected as shown below:

First page, line [57], under the title, ABSTRACT, the 4th line should read as, --tonitrile and triethylamine hydrochloride, treating the resulting material with triethylamine and recovering--.

Column 1, line 13, "an" should read --as--.

Column 2, line 54, should read as -- 3-(4-(((Trichloroethenyl)thio)phenyl)sulfonyl)-2- --.

Signed and Sealed this

Fourteenth Day of February 1978

[SEAL]

Attest:

RUTH C. MASON
Attesting Officer

LUTRELLE F. PARKER
Acting Commissioner of Patents and Trademarks